(12) United States Patent
Bayerköhler et al.

(10) Patent No.: US 6,849,286 B1
(45) Date of Patent: Feb. 1, 2005

(54) METHOD FOR PRODUCING A TABLET MADE OF ISOMALTULOSE, ISOMALT OR ISOMALT VARIANTS

(75) Inventors: Theodor Bayerköhler, Mannheim (DE); Tillmann Dörr, Hohen-Sülzen (DE); Jörg Kowalczyk, Bockenheim (DE); Markwart Kunz, Worms (DE); Peter Riffel, Mainz (DE)

(73) Assignee: Sudzucker Aktiengesellschaft Mannheim/Ochsenfurt, Mannheim (DE)

( * ) Notice: Subject to any disclaimer, the term of this patent is extended or adjusted under 35 U.S.C. 154(b) by 56 days.

(21) Appl. No.: 10/070,661

(22) PCT Filed: Sep. 9, 2000

(86) PCT No.: PCT/EP00/08832

§ 371 (c)(1),
(2), (4) Date: Jul. 9, 2002

(87) PCT Pub. No.: WO01/19401

PCT Pub. Date: Mar. 22, 2001

(30) Foreign Application Priority Data

Sep. 10, 1999 (DE) .......................................... 199 43 491

(51) Int. Cl.⁷ .................................................. A23P 1/02
(52) U.S. Cl. ...................... 426/285; 426/660; 514/960; 514/961
(58) Field of Search ................................ 426/285, 660; 554/960, 961

(56) References Cited

U.S. PATENT DOCUMENTS

| | | | | |
|---|---|---|---|---|
| 4,572,916 A | * | 2/1986 | Lindley et al. | 514/777 |
| 4,744,991 A | * | 5/1988 | Serpelloni | 426/5 |
| 4,980,189 A | * | 12/1990 | Keme et al. | 426/548 |
| 5,043,169 A | * | 8/1991 | Cherukuri et al. | 426/5 |
| 5,478,593 A | * | 12/1995 | Serpelloni et al. | 427/2.14 |
| 5,578,339 A | | 11/1996 | Kunz et al. | 426/658 |
| 5,709,895 A | * | 1/1998 | Tanaka et al. | 426/96 |
| 5,958,472 A | | 9/1999 | Robinson et al. | 426/3 |
| 6,039,813 A | * | 3/2000 | Pepper et al. | 127/42 |
| 6,165,511 A | | 12/2000 | Schwarz et al. | 424/489 |
| 6,224,904 B1 | | 5/2001 | Rapp et al. | 424/464 |
| 6,548,095 B1 | * | 4/2003 | Rapp et al. | 426/548 |
| 6,555,146 B1 | * | 4/2003 | Rapp et al. | 426/3 |
| 6,586,006 B2 | * | 7/2003 | Roser et al. | 424/484 |
| 6,669,963 B1 | * | 12/2003 | Kampinga | 424/499 |

FOREIGN PATENT DOCUMENTS

| | | | | |
|---|---|---|---|---|
| DE | 196 15 418 A1 | 10/1997 | ........... | C07C/31/18 |
| DE | 196 39 343 A1 | 4/1998 | ........... | A61K/9/20 |
| EP | 0 028 905 | 5/1981 | ........... | A61K/9/36 |
| EP | 0 625 578 A1 | 12/1993 | ........... | C12P/19/24 |
| NL | 0028905 | * | 5/1981 | |
| WO | WO92/02149 | * | 2/1992 | |
| WO | WO 92/10168 | | 6/1992 | ........... A61K/9/16 |
| WO | WO97/16078 | * | 5/1997 | |
| WO | WO 98/37769 | | 9/1998 | |

OTHER PUBLICATIONS

US PgPub 2003/0170185.*
US PgPub 2002/0187221.*
US PgPub 2003/0175396.*
US PgPub 2002/0028276.*

* cited by examiner

Primary Examiner—Carolyn Paden
(74) Attorney, Agent, or Firm—Finnegan, Henderson, Farabow, Garrett & Dunner, L.L.P.

(57) ABSTRACT

The present invention relates to a method of producing an improved compressed product, wherein agglomeration of the ingredients is induced. This invention also relates to a compressed product produced by this method.

17 Claims, 3 Drawing Sheets

METHOD FOR PRODUCING A TABLET MADE OF ISOMALTULOSE, ISOMALT OR ISOMALT VARIANTS

Figure 1:
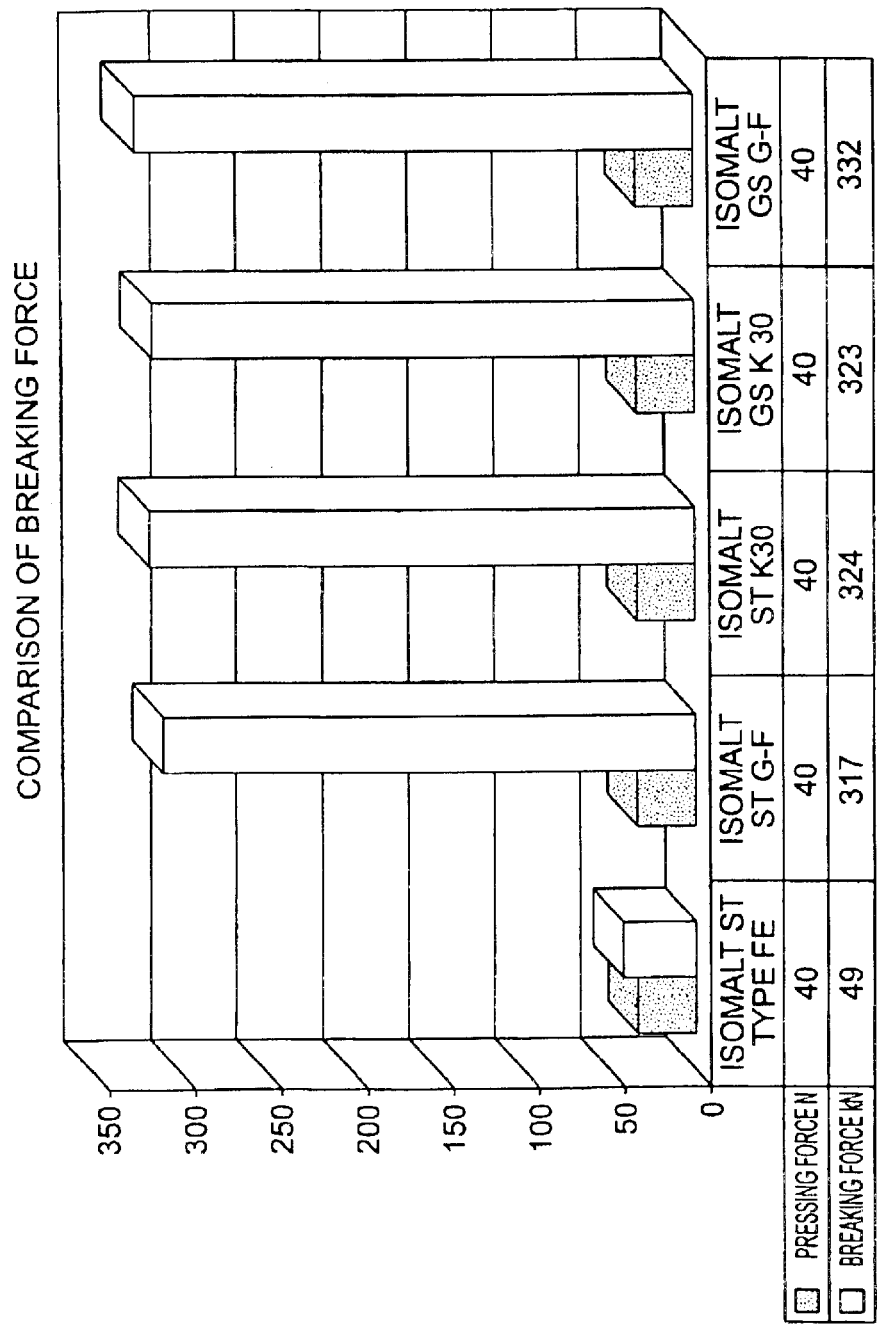

The present invention relates to a method of producing a compressed product of isomaltulose, isomalt and mixtures containing 1,6-GPS and 1,1-GPM, which are characterized by quantity ratios of 1,1-GPM to 1,6-GPS which differ from those of isomalt and/or which contain additional sugar alcohols, as well as the compressed products produced by this method.

Compressed products are foods, drugs, or semi-luxury items consisting of compressed ingredients. Compressed products accordingly generally contain a carrier or diluent, binders, lubricants or parting compounds as well as the active ingredients plus flavorings, pharmaceutical substances or sweeteners. Sucrose, lactose, glucose, starch or mannitol is often used as the carrier or diluent.

European Patent 0 028 905 B1 discloses tablets containing isomaltulose and methods of producing the same. This publication discloses an advantageous use of isomaltulose as a diluent for production of compressed products, because isomaltulose can be pressed directly without the use of a binder and without controlled granulation. According to this publication, crystalline isomaltulose produced directly by enzymatic conversion of sucrose to isomaltulose is used for tabletting.

German Patent 196 39 343 C2 discloses compressed products containing isomalt and isomalt variants. These compressed products are produced by simple pressing of the individual ingredients without a special mechanical and/or chemical treatment of the individual ingredients.

European Patent Application 0 625 578 A1 discloses isomalt variants, but they are not compressed products containing these sweeteners.

The compressed products containing isomaltulose, isomalt and isomalt variants known from the related art are all characterized by the required use of comparatively high compression pressures in production of the compressed product, but only a comparatively low tablet hardness can be achieved. In addition, the state-of-the art compressed products could also be improved with regard to their sensory properties; for example, they have a roughness when bitten into, and their fracture properties are not advantageous; furthermore, the dissolving properties in the mouth should also be improved.

The technical problem on which the present invention is based thus consists of a method of producing compressed products of isomaltulose, isomalt or mixtures containing 1,6-GPS and 1,1-GPM which are characterized by quantity ratios of 1,1-GMP to 1,6-GPS which differ from those of isomalt and/or contain other sugar alcohols and which overcome the disadvantages mentioned above, especially producing compressed products having a great hardness, improved sensory properties and improved fracture properties while using the lowest possible compression pressures.

The present invention solves the basic problem on which it is based by providing a method of producing a compressed product of isomaltulose, isomalt or mixtures containing 1,6-GPS and 1,1-GPM, characterized by quantity ratios of 1,1-GPM to 1,6-GPS which differ from those of isomalt and/or they contain other sugar alcohols, whereby in a first process step, the isomaltulose, the isomalt and/or the mixture containing 1,6-GPS and 1,1-GPM and having a maximum particle diameter $d_{90}$ of 100 μm ($d_{90}$=90% of the particles have the required diameter) is obtained or separated, and in a third process step, the separated ground fraction is agglomerated with the addition of a liquid binder, and then in a fourth process step the agglomerate is pressed to form a compressed product. The invention also solves the technical problem on which it is based by providing a compressed product and an agglomerate produced according to the present invention.

This invention thus provides for a compressed product to be produced from one or more of the educts isomaltulose, isomalt or mixtures containing 1,6-GPS and 1,1-GPM, which are characterized by quantity ratios of 1,1-GPM to 1,6-GPS which differ from those of isomalt and/or they contain other sugar alcohols; this is accomplished by dry milling one or more of the educts, whereby either after or during the milling, a fraction is separated and obtained whose maximum particle size is 100 μm. The adjustment of the primary particle size distribution according to this invention proves to be extremely important. Milling is preferably carried out in an air separation ball mill or a combination of a mill and a downstream air classifier. The . . . present invention may be a tablet, for example. The compressed products may contain additives and auxiliary substances such as lubricants, binders, diluents and flavorings, taste substances, parting compounds, coloring agents, acidifying agents, vitamins, functional foods, sweeteners and/or pharmaceutical substances.

In conjunction with the present invention, isomalt is understood to refer to an almost equimolar mixture of the two stereoisomers 6-O-α-D-glucopyranosyl-D-sorbitol (1,6-GPS) and 1-O-α-D-glucopyranosyl-D-mannitol (1,1-GPM), which is also known by the brand name Palatinit®. The term isomalt variant is understood to refer to mixtures containing 1,6-GPS and 1,1-GPM, which are characterized by quantity ratios of 1,6-GPM to 1,6-GPS, which differ from the quantity ratios of isomalt and/or contain other sugar alcohols such as 1,1-GPS (1-O-α-D-glucopyranosyl-D-sorbitol). Such mixtures are disclosed in European Patent Application 0 625 578 A1, for example, which is thus included in the disclosure content of the present patent application with regard to the quantitative and qualitative composition of sugar alcohol mixtures containing 1,1-GPM and 1,6-GPS and methods of producing the same. Therefore, the isomalt variants may be, for example, mixtures of 10 wt % to 50 wt % 1,6-GPS, 2 wt % to 20 wt % 1,1-GPS and 30 wt % to 70 wt % 1,1-GPM, or mixtures of 5 wt % to 10 wt % 1,6-GPS, 30 wt % to 40 wt % 1,1-GPS and 45 wt % to 60 wt % 1,1-GPM. According to the preceding discussion, isomalt variants may also be mixtures enriched with 1,6-GPS or 1,1-GPM, i.e., mixtures such as those described in German Patent 195 32 396 C2, which are also included in the disclosure content of the present patent application with regard to the quantitative and qualitative composition of the mixtures described there and methods of producing the same. Mixtures enriched with 1,6-GPS are characterized by a 1,6-GPS content of 57 wt % to 99 wt % and a 1,1-GPM content of 43 wt % to 1 wt %, while mixtures containing 1,1-GPM are characterized by a 1,6-GPS content of 1 wt % to 43 foods, sweeteners and/or pharmaceutical substances contain [ . . . ]

In conjunction with the present invention, isomalt is understood to refer to an almost equimolar mixture of the two stereoisomers 6-O-α-D-glucopyranosyl-D-sorbitol (1,6-GPS) and 1-O-α-D-glucopyranosyl-D-mannitol (1,1-GPM), which is also known by the brand name Palatinit®. Mixtures containing 1,6-GPS and 1,1-GPM, which are characterized by quantity ratios of 1,1-GPM to 1,6-GPS which differ from the quantity ratios of isomalt and/or contain other sugar alcohols such as 1,1-GPS (1-O-α-D-glucopyranosyl- D-sorbitol) and are also refered to as isomalt variants, are described, for example, in European Patent Application 0 625 578 A1, which is thus included in the disclosure content of the present patent application with regard to the quantitative and qualitative composition of sugar alcohol mixtures containing 1,1-GPM and 1,6-GPS and methods of producing them. Therefore, such mixtures may be, for example, mixtures of 10 wt % to 50 wt % 1,6-GPS, 2 wt % to 20 wt % 1,1-GPS and 30 wt % to 70 wt % 1,1-GPM, or mixtures of 5 wt % to 10 wt % 1,6-GPS, 30 wt % to 40 wt % 1,1-GPS and 45 wt % to 60 wt % 1,1-GPM. According to the preceding discussion, such mixtures may also be mixtures enriched with 1,6-GPS or 1,1-GPM, i.e., mixtures such as those described in German Patent 195 32 396 C2, which are also included in the disclosure content of the present patent application with regard to the quantitative and qualitative composition of the mixtures described there and methods of producing the same. Mixtures enriched with 1,6-GPS are characterized by a 1,6-GPS content of 57 wt % to 99 wt % and a 1,1-GPM content of 43 wt % to 1 wt %, while mixtures containing 1,1-GPM are characterized by a 1,6-GPS content of 1 wt % to 43 wt % and a 1,1-GPM content of 57 wt % to 99 wt %. The mixtures containing 1,6-GPS and 1,1-GPM mentioned above may also contain other substances such as mannitol, sorbitol, hydrogenated or non-hydrogenated oligosaccharides as well as optionally glucose, fructose and/or sucrose, trehalulose or isomaltose.

This invention thus provides that according to a first procedure step the educt, namely isomaltulose, isomalt and/or the mixtures containing 1,6-GPS and 1,1-GPM, is milled while dry. In a preferred embodiment of this invention, this can take place in an air separation ball mill or a combination of a mill and a downstream air classifier. This invention also proposes that the educts used be adjusted to the required particle size by measures other than milling, e.g., by crushing. Additives and auxiliary substances may be added in milling, preferably in an amount of up to 30 wt % (based on total dry solids).

In a second process step which takes place essentially concurrently or subsequently following milling, this invention provides for the fraction to be separated and for further processing to be performed, where the particles contained in this fraction should have a maximum size of 100 μm, preferably less than 50 μm, especially having a maximum size of 40 μm. ° Celsius, into the fluidized bed. Depending on the binder used, the temperature of the binder should be selected so that the binder is sprayable, i.e., the temperature is at or above the melting point of the binder. Following agglomeration, in another preferred embodiment of this invention, drying may be performed; in another preferred embodiment, the drying is performed at a constant incoming air temperature, e.g., 70° Celsius to 90° Celsius, especially preferably 80° Celsius. In another preferred embodiment, the drying may be carried out at an exhaust air temperature up to 50° Celsius to 70° Celsius, preferably 60° Celsius, with product cooling preferably being accomplished with outside air.

This invention of course also relates to the agglomerates themselves produced as described above.

In another advantageous embodiment of the present teaching, this invention provides for a size fractionation to be performed on the agglomerated products after adding the binder and agglomerating but before pressing the agglomerate, especially by separating oversized particles and fines. A screen machine preferably with a screen lining of 0.8 mm to 0.1 mm may preferably be provided.

In a fourth process step according to this invention, the agglomerated product, optionally fractionated after agglomeration, is pressed directly. Additives or auxiliary substances such as lubricants or parting compounds, active ingredients, etc. may be added to the agglomerates. Such substances may include sweeteners, flavorings, taste substances and coloring agents, food-compatible acids, disintegrants, monosaccharides, disaccharides, monosaccharide alcohols, disaccharide alcohols, starch, starch derivatives, pectin, polyvinylpyrrolidone, cellulose, cellulose derivatives, stearic acid or the salts thereof, or inulin, oligofructose or other products such as functional foods, which may be offered accordingly. Sorbitol, mannitol, hydrogenated or non-hydrogenated oligosaccharides, erythritol, xylitol or sugars such as sucrose, glucose, lactose, fructose or xylose may also be added to the agglomerates. In an advantageous manner, the amount of these substances, based on the total dry weight, is less than or equal to 30 wt %, preferably less than 25 wt %, 20 wt %, 15 wt %, 10 wt % or 5 wt %. These additives and auxiliary substances may of course also be added to the educts during milling. In another embodiment, the components mentioned above, such as additives or auxiliary substances, e.g., erythritol, may also be ground dry together with the isomaltulose, isomalt and/or isomalt variant and then treated further according to this invention. In another embodiment of the present invention, the above-mentioned additives or auxiliary substances such as erythritol may be dissolved in a solvent, such as water, and sprayed into the ground fraction during the agglomeration of the ground isomaltulose, isomalt and/or isomalt variant, so that introduction of the dissolved additives or auxiliary substances takes place during the agglomeration process. Finally, in a third embodiment of this invention, these additives or auxiliary substances may be mixed with the agglomerated fraction and pressed to form a compressed product.

In an especially advantageous embodiment, the compressed products produced according to this invention are sugar-free. In another embodiment, the compressed products or agglomerates may also be xylitol-free. In another preferred embodiment, the compressed products according to this invention may be reduced-calorie products, suitable for diabetics, anti-lipidemic, bi-fidogenic and/or non-cariogenic.

Furthermore, the agglomerates or educts may also contain intense sweeteners such as dipeptide sweeteners, saccharine, acesulfame K, aspartame, cyclamate, glycyrrhizine, thaumatin, saccharin, steveoside, neohesperidin dihydrochalcone and/or sucralose.

In an advantageous manner, the compressed products according to this invention also contain taste or flavoring substances such as lemon flavoring or peppermint flavoring. The compressed products according to this invention may also contain food-compatible acids such as ascorbic acid or citric acid and also fatty acids or their salts such as magnesium stearate or sodium stearate as lubricants. Finally, the compressed products according to this invention may also contain coloring agents and/or disintegrants such as bicarbonate or carboxymethylcellulose.

In an especially preferred embodiment, the compressed products that are produced can introduce active pharmaceutical ingredients into the mouth and throat area and release them there. In conjunction with the present invention, active pharmaceutical ingredients are understood to refer to substances that have a desired prophylactic or therapeutic effect on the human or animal body. These substances are thus used in particular to prevent or treat deficiency states or disease syndromes. According to this invention, for example, enzymes, coenzymes, minerals, vitamins, antibiotics, microbicidal or fungicidal substances, nicotine, caffeine, zinc, eucalyptus, menthol, codeine, phenacetin, aspirin or other active pharmaceutical substances may be incorporated into the compressed products. The active pharmaceutical ingredients are to be provided in an amount that will have the desired pharmaceutical effect. The processability of the compressed products under gentle conditions makes the compressed products according to this invention especially suitable for introducing active pharmaceutical ingredients into the mouth and throat area.

This invention also relates to the compressed products produced by the method according to this invention, especially in the form of lozenges, chewable tablets or effervescent tablets.

Other advantageous embodiments of this invention are derived from the subclaims.

The following examples are presented to illustrate this invention in detail.

Figure 2:
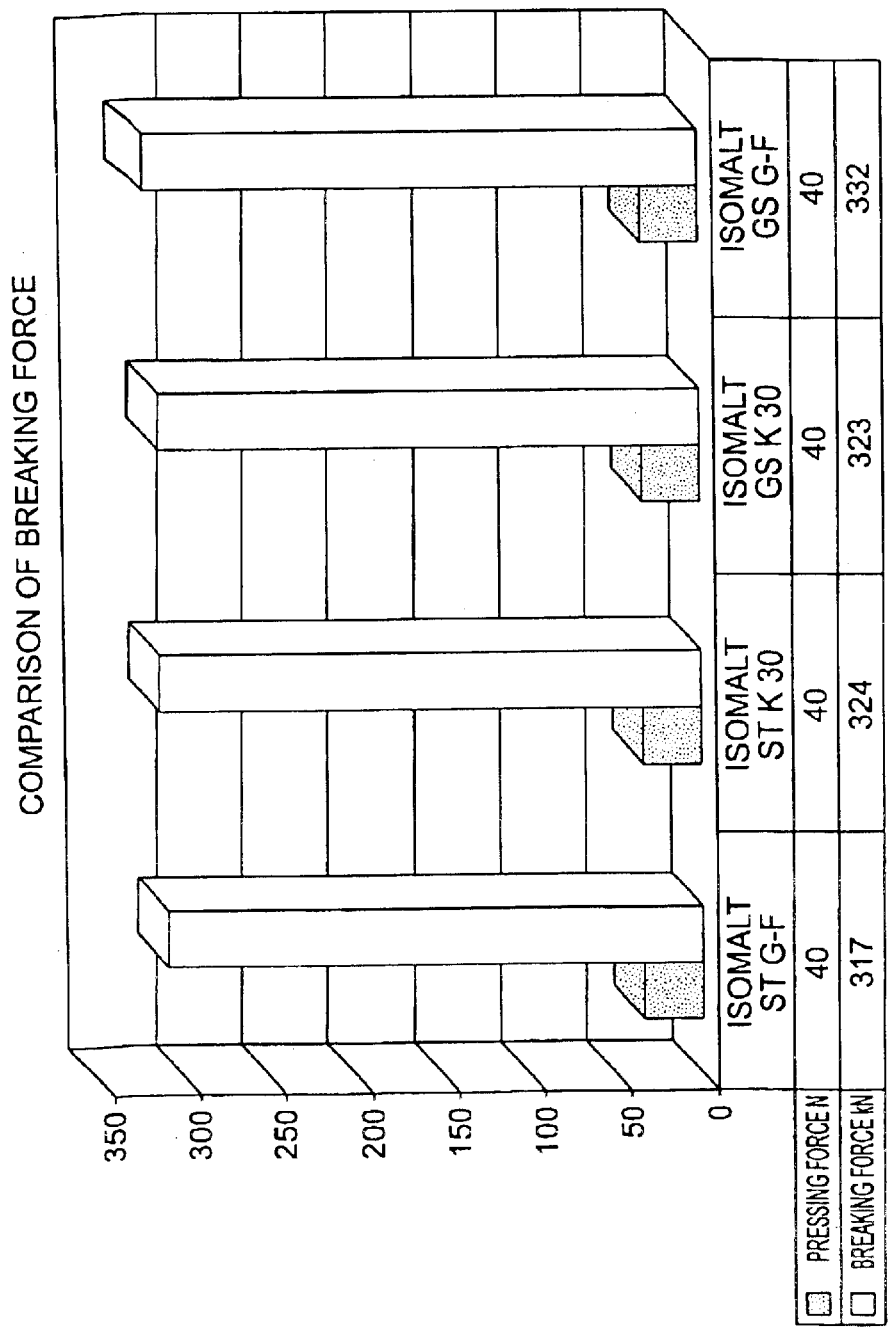
Figure 3:
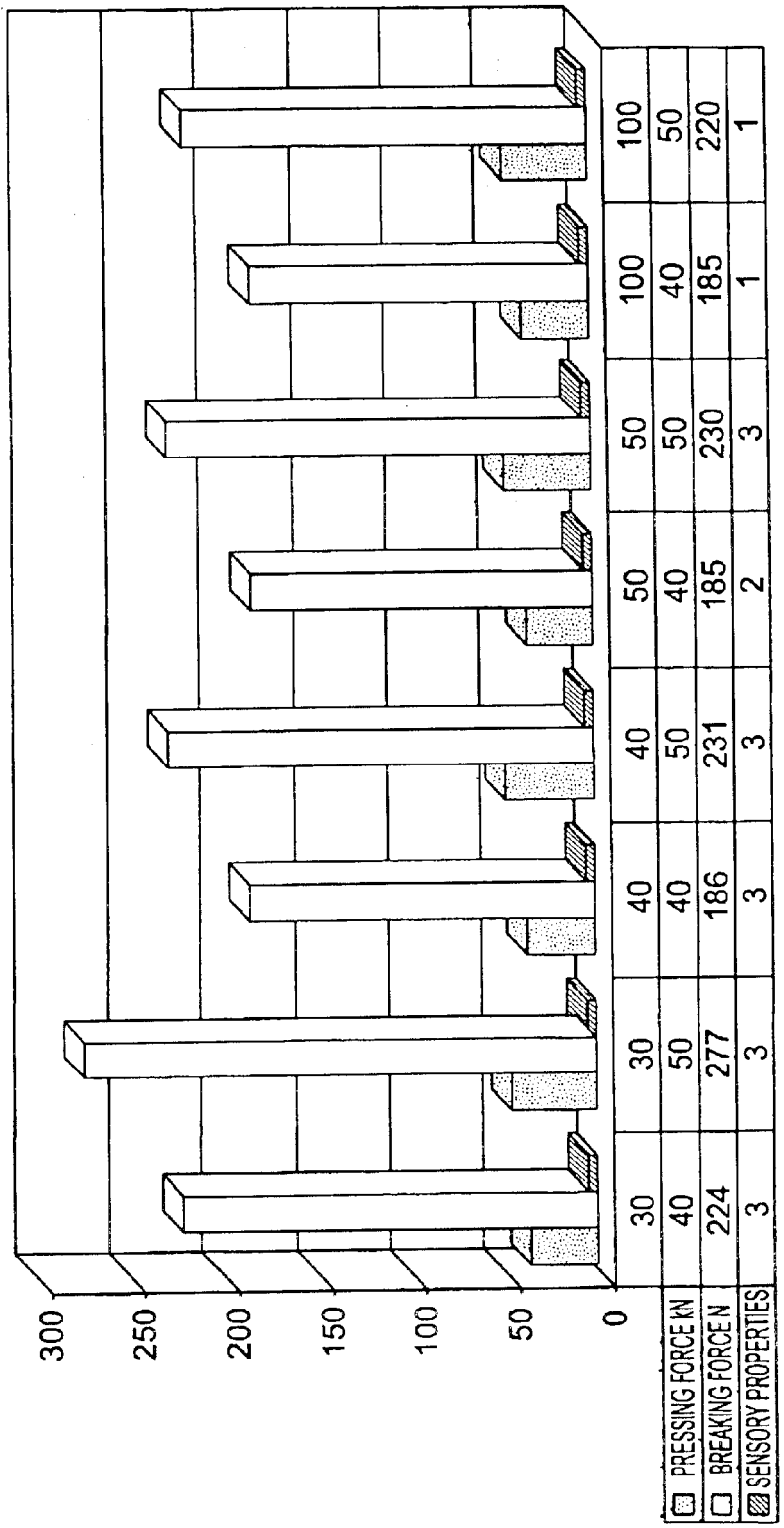

The figures show:

FIG. 1 a comparison of the breaking force between compressed products of isomalt ST (type FE, not agglomerated), isomalt ST (agglomerated) and isomalt GS (agglomerated), FIG. 2 a comparison of the breaking force between compressed products of isomalt ST and isomalt GS, and FIG. 3 breaking force information on compressed products containing isomaltulose.

EXAMPLE 1

Production of Compressed Products

Isomalt ST (standard, an almost equimolar mixture of 1,1-GPM and 1,6-GPS) was milled dry in an air separation ball mill to a particle size of $d_{90}=50\,\mu m$. The same procedure was followed with isomalt GS (composition approx. 76% 1,6-GPS and 23% 1,1-GPM) and isomaltulose. Isomalt ST type FE (like isomalt ST, but not agglomerated, particle size 60 $\mu m$ to 300 $\mu m$) was used as the control.

To prepare the agglomerates, a fluidized bed agglomerator, namely the STREA 7 agglomerator from Aeromatic, was used in a batch-type process. The experimental batches each amounted to 10 kg. The ground bulk material was placed in the fluidized bed agglomerator and a fluidized bed was established at approx. 60° C. On reaching this temperature, a binder solution at approx. 75° C. was sprayed into the fluidized bed, using either 3 wt % collidone or 0.8 wt % gelatin (130 Bloom) and 0.5 wt % fat. The spray pressure used was between 2.0 and 4.5 bar, with an admission pressure of 0.4 to 0.8 bar being used. Then the agglomerates that were formed were dried at a constant incoming air temperature of approx. 80° Celsius up to an exhaust air temperature of approx. 60° Celsius, followed by cooling of the product with outside air. Then size fractionation was performed with an oscillating screening machine with a screen lining of 0.8 mm to 0.1 mm, separating the oversized particles and the fines. Agglomerate fractions with a particle diameter of 20.1 mm to ≦0.8 mm were then used further to produce the compressed products after adding flavorings, intense sweeteners and parting compounds according to the following recipe.

Recipe:

| Isomalt, isomalt variant (GS) or isomaltulose agglomerate | 98.40% |
|---|---|
| Mg stearate | 0.50% |
| Natural lemon flavor | 0.50% |
| Citric acid (mono) | 0.30% |
| Acesulfame K | 0.15% |
| Aspartame | 0.15% |

All the amounts are given in wt %, based on the total dry weight of the compressed product.

The following table shows physicochemical parameters of the compressed product mixtures used here.

TABLE (K: collidone 30; G-F: gelatin fat)

| Recipe | Water content % | $d_{05}$ mm | $d_{95}$ mm | d' mm | n | Bulk density g/cm$^3$ | Tamped density g/cm$^3$ | Flow time S |
|---|---|---|---|---|---|---|---|---|
| Isomalt ST (K) | 4.1 | 0.53 | 0.07 | 0.31 | 2.01 | 0.44 | 0.45 | 23.0 |
| Isomalt ST (G-F) | 3.9 | 0.53 | 0.06 | 0.3 | 1.88 | 0.51 | 0.52 | 24.7 |
| Isomalt GS (K) | 1.9 | 0.53 | 0.06 | 0.3 | 1.92 | 0.42 | 0.42 | 24.6 |
| Isomalt GS (G-F) | 1.4 | 0.7 | 0.09 | 0.4 | 1.94 | 0.53 | 0.54 | 18.9 |
| Isomaltulose (K) | 5.1 | 0.53 | 0.04 | 0.26 | 1.55 | 0.44 | 0.45 | 22.8 |

The pourability and the flow time were determined according to DIN 53194 and DIN 53492.

Type of nozzle for determining pourability:
10 mm diameter

The bulk density and tamped [density] were determined according to DIN 53194.

The mixtures defined above for the compressed product experiments were produced in the ploughshare mixer from Lodige. The mixing time was 1.5 minutes. The individual ingredients were added through an opening in the cover flap on the mixer. After conclusion of the mixing operation, the mixtures were poured into PE bags of 5 kg each and sealed.

Round tablets having a diameter of 18 mm and facets, a web height of 0.35 to 0.37 mm and a weight between 850 mg and 1000 mg were then produced with the resulting mixtures by using a Fette PT 2090 rotary press.

EXAMPLE 2

Comparison of the Breaking Force

FIG. 1 shows a breaking force comparison between compressed products made of isomalt ST (K and G-F) and agglomerated isomalt GS (K and G-F). For comparison, a compressed product of isomalt ST type FE is also shown; it was produced from a fraction of particles with a particle diameter of 60 $\mu m$ to 300 $\mu m$. The compressed products according to this invention were produced with a pressing force of only 40 kN, but they had an extremely high breaking force. (The abbreviations in the figures denote: K 30=collidone 30, GF=gelatin-fat).

FIG. 2 shows a breaking force comparison between isomalt ST and isomalt GS, both in agglomerated form. It can be seen here that there is no significant difference between these two forms of isomalt. In a sensory evaluation, the dissolving properties of the GS variant in the mouth were evaluated as slightly better.

FIG. 3 compares compressed products produced on the basis of isomaltulose (same as palatinose). This shows the pressing force, the breaking force and the sensory properties of isomaltulose compressed products produced from a fraction having a particle size of 100=m and collidone 30. The use of a fraction having particles with a diameter of ≦100 μm n preferably ≦50 μm, especially ≦30 μm, is especially important in the case of isomaltulose, because isomaltulose fractions with particle sizes>100 μm show a marked tendency toward a perceptibly rough surface in compression.

The results presented above show that the agglomeration specified according to this invention results in the fact that much lower pressing forces can be used than in the related art to produce tablets with a sufficient breaking force. The mixture with the agglomerates produced in this way leads to improved flowability and a smaller fines fraction, which in turn leads to improved processability and reduced machine wear as well as an increased tabletting output.

What is claimed is:

1. A method of producing a compressed product of isomaltulose, isomalt or mixtures containing 6-O-α-D-glucopyranosyl-D-sorbitol ("1,6-GPS") and 1-O-α-D-glucopyranosyl-D-mannitol ("1,1-GPM"), which are characterized by quantity ratios of 1,1-GPM to 1,6-GPS which differ from those of isomalt and/or contain other sugar alcohols, comprising a) dry grinding the isomaltulose, isomalt and/or the mixture containing 1,6-GPS and 1,1-GPM,
   b) at the same time or thereafter, separating or obtaining a ground fraction of the isomaltulose, the isomalt or the mixture containing 1,6-GPS and 1,1-GPM with a maximum particle diameter of 100 μm,
   c) agglomerating the ground fraction with the addition of a liquid binder, and
   d) then compressing the mixture to form a compressed product.

2. The method according to claim 1, wherein the mixture containing 1,6-GPS and 1,1-GPM is a mixture of 10 wt % to 50 wt % 1,6-GPS, 2 wt % to 20 wt % 1,1-GPS and 30 wt % to 70 wt % 1,1-GPM, or a mixture of 5 wt % to 10 wt % 1,6-GPS, 30 wt % to 40 wt % 1,1-GPS and 45 wt % to 60 wt % 1,1-GPM, or a mixture enriched with 1,6-GPS with a 1,6-GPS content of 57 wt % to 99 wt % and a 1,1-GPM content of 43 wt % to 1 wt % or a mixture enriched with 1,1-GPM with a 1,6-GPS content of 1 wt % to 43 wt % and a 1,1-GPM content of 57 wt % to 99 wt %.

3. The method according to claim 1, wherein the particle diameter is ≦50 μm.

4. The method according to claim 1, wherein the particle diameter is ≦30 μm.

5. The method according to claim 1, wherein the milling is performed in an air separation ball mill or in a combination of a mill and a downstream air classifier.

6. The method according to claim 1, wherein additives or auxiliary substances are introduced during milling.

7. The method according to claim 1, wherein the liquid binder is a solution or suspension of isomalt, a mixture containing 1,6-GPS and 1,1-GPM characterized by quantity ratios of 1,1-GPM to 1,6-GPS which differ from those of isomalt, and also containing fat and gelatin or collidone.

8. The method according to claim 1, wherein the liquid binder is added to the separated ground fraction by spraying.

9. The method according to claim 1, wherein the liquid binder is added to the separated ground fraction through a nozzle.

10. The method according to claim 1, wherein agglomeration is performed intermittently in a fluidized-bed agglomerator or in a continuously operated installation.

11. The method according to claim 1, wherein the liquid binder is added to the separated ground fraction in a form in which it is heated to a temperature above room temperature.

12. The method according to claim 1, wherein additives and/or flavorings are added to the agglomerate after adding the liquid binder and before pressing.

13. The method according to claim 1, wherein size fractionation of the agglomerate is performed after adding the liquid binder and before pressing.

14. The method according to claim 13, wherein the size fractionation of the agglomerate is performed in a screening machine.

15. The method according to claim 1, wherein the agglomerate is dried after agglomeration.

16. A compressed product that can be produced according to claim 1.

17. An agglomerate that can be produced by process steps a) through c) according to claim 1.

* * * * *

UNITED STATES PATENT AND TRADEMARK OFFICE
CERTIFICATE OF CORRECTION

PATENT NO. : 6,849,286 B1
APPLICATION NO. : 10/070661
DATED : February 1, 2005
INVENTOR(S) : Theodor Bayerköhler et al.

It is certified that error appears in the above-identified patent and that said Letters Patent is hereby corrected as shown below:

Column 3, line 44, after "size of 40 μm" insert:

--, preferably 35 μm and especially preferably 30 μm. If after the first process step, i.e., milling, the educt used already has the required particle size $d_{90}$ ($d_{90}$ = 90% of the particles having the required particle diameter), then the separation may be omitted and the resulting powder sent directly to the third process step. The milling and separating may of course take place at the same time, e.g., in an air separation ball mill or a combination of a mill and a downstream air classifier.

In conjunction with the present invention, a maximum particle diameter of 100 μm, 40 μm, 35 μm or 30 μm is understood to indicate that at least 90% of the particles ($d_{90}$) of the ground fraction have a maximum diameter of 100 μm, 40 μm, 35 μm or 30 μm.

In a third process step, this invention provides for a liquid binder to be added to the ground fraction that is separated. In an especially preferred embodiment of this invention, this liquid binder is a solution or suspension of isomalt, an isomalt variant, especially an aqueous solution or suspension, a mixture of gelatin and fat, a water-soluble colloid, such as polyvinylpyrrolidone (e.g., Kollidon® from BASF), starch, sugars such as sucrose, dextrose, lactose, natural or synthetic gums such as gum arabic, cellulose, talc, microcrystalline cellulose, polymerized reducing sugars, pectin, preservative, agar, acidifying agents, insulin, alkali carboxymethylcellulose, HSH (hydrogenated starch hydrolysate), polydextrose in partially or completely purified form and/or in partially or completely neutralized form, sodium carboxymethylcellulose, etc. Other binders may of course also be used, preferably physiologically compatible and/or non-cariogenic, reduced-calorie binders. In an advantageous manner, the compressed product according to this invention contains 0.5 wt% to 7 wt% of the binder or a combination of binders, preferably 2 wt% to 3 wt%.

Signed and Sealed this

Fifteenth Day of June, 2010

David J. Kappos
*Director of the United States Patent and Trademark Office*

In another preferred embodiment of this invention, the liquid binder, which is preferably in the form of an aqueous solution or aqueous suspension, is added to the ground educt by spraying through a nozzle system.

The agglomerates formed after mixing the educt with the binder may be produced preferably in a fluidized bed agglomerator, especially preferably in a batch-wise process or in a continuous installation. It is preferable according to this invention to establish a fluidized bed at a temperature of 50 °Celsius to 70 °Celsius, especially 60 °Celsius, and on reaching the desired temperature, to spray the binder solution or binder suspension heated to approx. 70 °Celsius to 80 °Celsius, preferably 75--.